(12) United States Patent
Guttieri et al.

(10) Patent No.: US 7,795,015 B2
(45) Date of Patent: Sep. 14, 2010

(54) ANTIBODIES EXPRESSED IN INSECT CELLS

(75) Inventors: Mary C. Guttieri, Myersville, MD (US); Connie S. Schmaljohn, Frederick, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 10/094,546

(22) Filed: Mar. 8, 2002

(65) Prior Publication Data

US 2002/0197677 A1    Dec. 26, 2002

Related U.S. Application Data

(60) Provisional application No. 60/274,164, filed on Mar. 8, 2001.

(51) Int. Cl.
*C12N 15/63* (2006.01)
*C07K 16/00* (2006.01)

(52) U.S. Cl. .................................. 435/320.1; 530/387.1

(58) Field of Classification Search ................. 435/69.1, 435/69.7, 320.1, 235.1, 471, 455, 325; 536/23.1, 536/24.1, 23.4; 500/387.1

See application file for complete search history.

(56) References Cited

U.S. PATENT DOCUMENTS

| 5,766,939 | A * | 6/1998 | Conneely et al. | 435/320.1 |
| 2003/0148340 | A1 * | 8/2003 | Harney et al. | 435/6 |
| 2005/0238645 | A1 * | 10/2005 | Gold et al. | 424/144.1 |

OTHER PUBLICATIONS

Hsu, et al. J. Biological Chemistry, 1997, vol. 272, No. 14, pp. 9062-9070.*
Gutteiri, et al. Journal of Immunological Methods, 2000, vol. 246, pp. 97-108.*
Jarvis et al. Immediate-early baculovirus vectors for foreign gene expression in transformed or infected insect cells. Protein Expr Purif. Sep. 1996;8(2):191-203.*
Liang et al. Baculovirus expression cassette vectors for rapid production of complete human IgG from phage display selected antibody fragments. J Immunol Methods. Jan. 1, 2001;247(1-2):119-30.*

* cited by examiner

*Primary Examiner*—Michele K Joike
(74) *Attorney, Agent, or Firm*—Elizabeth Arwine

(57) ABSTRACT

Three vectors are described which allow the conversion of Fab fragments into or single chain Fv fragments into full-length antibody molecules. Methods for using the vectors and the resulting antibodies are also described.

10 Claims, 11 Drawing Sheets

Fig. 3

A

Figure 1:
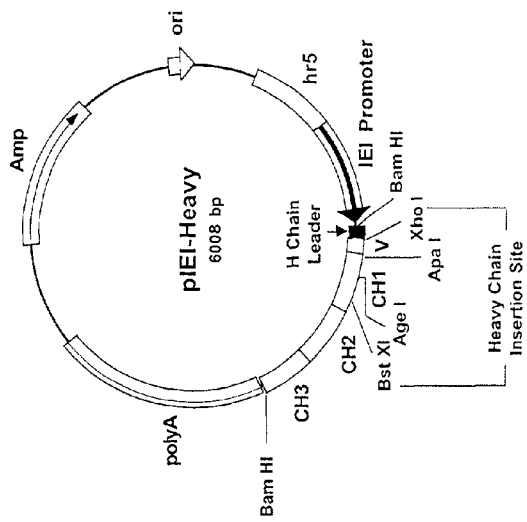
Figure 1:
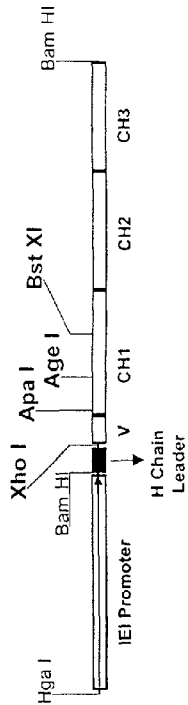
Figure 1:
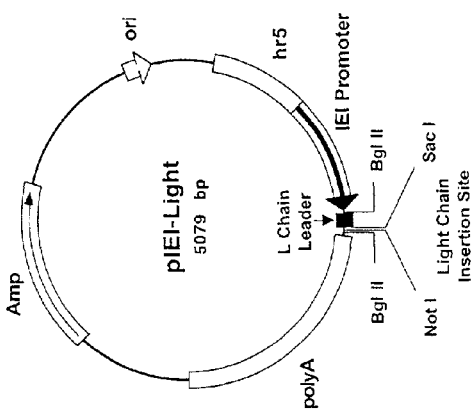
Figure 1:
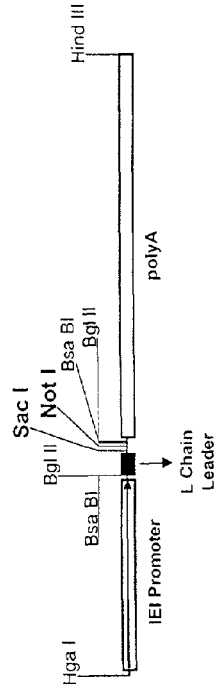

- Mouse mAb BD01 to HTNV
- Human mAb 3B to HTNV
- Human mAb A12 to PUUV

B

- Mouse mAb 5B3 to VACV
- Mouse mAb 5B8 to VACV
- Human mAb 14B to VACV
- Mouse mAb BD01 to HTNV

Fig. 4

Fig. 6

Cassette Vectors for Conversion of Mouse or Human V Regions to Complete Chimeric or Human IgG

ELISA with Insect Cell-Expressed Chimeric IgG to HTNV G1-Protein

Fig. 10A

ELISA with Insect Cell-Expressed Chimeric IgG to HTNV G2-Protein

Fig. 10B

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: linker sequence

<400> SEQUENCE: 1
gatgggccct tggtggaggc                                            20

<210> SEQ ID NO 2
<211> LENGTH: 30
<212> TYPE: DNA
<213> ORGANISM: Artificial sequence
<220> FEATURE:
<223> OTHER INFORMATION: primer sequence

<400> SEQUENCE: 2
cattgtccgt gtgcgctagc atgcccgtaa                                 30

<210> SEQ ID NO 3
<211> LENGTH: 39
<212> TYPE: DNA
<213> ORGANISM: Artificial sequence
<220> FEATURE:

-continued

```
<223> OTHER INFORMATION: primer sequence

<400> SEQUENCE: 3
tagtcgcgag cgagctcctg ggcccaggac cctgtgcag                              39

<210> SEQ ID NO 4
<211> LENGTH: 39
<212> TYPE: DNA
<213> ORGANISM: Artificial sequence
<220> FEATURE:
<223> OTHER INFORMATION: primer sequence

<400> SEQUENCE: 4
cgcagatcta gctcgagcag ttgcacctca cactggaca                              39
```

ANTIBODIES EXPRESSED IN INSECT CELLS

This application claims priority under 35 U.S.C. from provisional application serial No. 60/274,164 filed on Mar. 8, 2001.

FIELD OF THE INVENTION

The present invention relates generally to the preparation in insect cells of high yield, purified bioactive antibodies.

INTRODUCTION

Antibody therapy has proven to be a valuable tool in the treatment of human disease by supplementing the natural immune response to pathogens (Levy, 2000, Semin. Hematol. 37, 4-6; Sawyer, 2000, Antiviral Res. 47, 57-77). Due to their immunogenicity in humans, rodent-derived immunoglobulins are less suitable for this purpose than human antibodies. Prior to the advent of recombinant DNA technology, it was necessary to obtain human antibodies for therapy from serum pools via an expensive process yielding non-reproducible samples potentially contaminated with adventitious agents such as hepatitis virus. Today, recombinant DNA techniques offer a means for producing human monoclonal antibodies (MAbs) that circumvent these problems. It is difficult, though, to obtain human antibody genes, and as a result, researchers have often relied on complicated methods such as those that humanize murine MAbs (Wu et al., 1999, J. Mol. Biol. 294, 151-162) or use transgenic mice (Wells, 2000, Chem. Biol. 7, R185-186). However, technology is now available that offers a more simplistic approach by using a phage display, bacterial expression system for the generation and selection of Fab or single chain (sc) Fv antibody fragments (Barbas and Lerner, 1991 Proc. Natl. Acad. Sci. USA 88, 7978-7982; Sheets et al., 1998, Proc. Natl. Acad. Sci. USA 95, 6157-6162).

Phage display technology allows for the construction of large combinatorial antibody libraries and has been used to isolate human MAb fragments to a variety of pathogens (Burton, 1991, Trends Biotechnol. 9, 169-175; Hoogenboom et al., 1998, Immunotechnology 4, 1-20; Liang et al., 1996, Virology 217, 262-271 Schmaljohn et al., 1999, Virology 258, 189-200; Williamson et al., 1993, Proc. Natl. Acad. Sci. USA 90, 4141-4145). However, the fragments generated in this manner do not possess the Fc domain of the antibody associated with several important immune functions, including complement activation and opsonization. Furthermore, Fabs and scFvs exhibit a short serum half-life in the human body (Sharkey et al., 1991, Cancer Res. 51, 3102-3107; Vieira and Rajewsky, 1988, Eur. J. Immunol. 18, 313-316). Full-length antibodies are, therefore, more desirable for immune therapy, and as a result, methods for converting antibody fragments to complete immunoglobulins are required.

Cassette vectors for expression of full-length human antibodies using Fab fragments have previously been described for mammalian and baculovirus expression systems (Bender et al., 1993, Hum. Antibod. Hybridomas 4, 74-79; Poul et al., 1995a, Eur. J. Immunol. 25, 2005-2009; Poul et al., 1995b, Immunotechnology 1, 189-196). Although mammalian cells offer the advantage of producing authentically processed and folded proteins, the methods used to generate transformants capable of expressing the desired antibody are time consuming and expensive. Baculovirus expression systems are an attractive alternative, capable of generating high yields of intact and biologically functional IgG. However, baculovirus infection culminates in death of the host cell, thereby allowing for only transient antibody expression. In addition, the host's secretory pathway can become impaired during the late phase of infection further limiting productive expression (Jarvis and Summers, 1989, Mol. Cell Biol. 9, 214-223).

Therefore, there is a need for a method for producing full-length antibodies using antibody fragments and a convenient system that allows for continuous production of biologically functional IgG.

SUMMARY OF THE INVENTION

The present invention satisfies the need discussed above. In this application is described a method that allows for the continuous expression of biologically functional human IgG from stably-transformed insect cell genomes. When compared to mammalian expression systems, insect cell-mediated expression is in its infancy since little is known about the mechanism of integration of genes into the insect cell genome and the location of insertion sites, or what cis- or trans-acting sequences could be used to up-regulate transcription after integration has occurred and/or that will improve integration or insertion into sites favorable for transcription. This is reflected by the fact that the concentration of expressed protein recovered from transformed insect cells is considerably lower than that obtained from mammalian or baculovirus expression systems. Although sufficient quantities of expressed protein are obtained for in vitro analysis, the concentration is not sufficient to support in vivo studies (e.g. protective efficacy in animal models). In addition, we needed to confirm that the differences in glycosylation of the expressed molecule when compared to the mammalian counterpart did not affect important IgG activities, including complement lysis activity and antibody-dependent cell-mediated cytotoxicity.

However, we found that insect cell expression provides a safer means to produce therapeutic proteins since insect cells do not possess factors, associated with mammalian cells, that can be potentially harmful to humans (e.g., retroviral elements etc.). In addition, transformed insect cells generate a continuous and consistent supply of antibody which offers an advantage over the transient baculovirus expression system.

Using this technology, we present here the first cassette vector system for conversion of human Fabs from combinatorial libraries to complete IgG1 monoclonal antibodies in stably-transformed insect cells. We engineered two transfer vectors, pIE1-Light and pIE1-Heavy, that permit joining of coding regions for light chain and heavy chain variable regions of human Fabs selected from phage display libraries to human signal sequences and the constant domains of human IgG1. Sequences encoding heavy chain variable regions of human Fabs of other subtypes or classes (e.g. IgG2, IgG3, IgM, IgA etc.) can also be cloned in-frame into the cassette vector of the present invention to produce IgG1 antibodies. This methodology utilizes a universal and rapid direct cloning method provided by convenient restriction enzyme sites within the vectors.

After confirming that antibody genes inserted into the genomes of insect cells can be expressed and that the MAb produced in this manner is functional, i.e. can bind and neutralize virus (Guttieri et al., 2000, J. Immunol. Methods 246, 97-108), we tested and demonstrated the efficacy of this system by using our constructs to transform insect cells with genes coding for human MAbs using sequences derived from Fabs selected from phage display libraries. Antibody genes are inserted into the insect cell chromosome under control of the baculovirus immediate early gene promoter, IEI, which is recognized by the insect cell RNA polymerase (Jarvis et al., 1990, Biotechnology 8, 950-955; Jarvis et al., 1996, Protein Expr. Purif. 8, 191-203). Our data indicate that the expressed antibodies are complete and biologically functional. As a result, this cassette vector system provides a feasible and efficacious means for the generation of human antibodies of potential therapeutic value.

In addition, we engineered a plasmid cassette vector, pAc-V-Light, that when used in conjuction with vector pIE1-Heavy, can convert human or murine variable regions comprising antibody fragments, such as single chain Fv (scFv), to complete human or mouse/human chimeric IgG1 MAbs in stably transformed insect cells. This is very useful for creating a completly human MAb from a mouse MAb. Normally, the steps required to do this are very labor intensive. These steps, though, are reduced by using our cassette vector system since this system provides for conversion of the constant domains of the antibody, and as a result, one will then only need contend with converting the variable regions.

This vector contains coding sequences for light-chain constant regions as well as convenient restriction sites that permit joining of the coding regions for the variable domains of antibody fragments. The light chain antibody gene, once generated, is subcloned into a vector expressible in insect cells and, along with a vector, such as pIE1-Heavy, -Heavy, expressing the heavy chain genes, used to transform insect cells for antibody production. To test this system, we cloned the variable domains of two murine HTNV-specific, Fab antibody fragments into our constructs then used the complete light and heavy chain vectors to generate transformed insect cell lines capable of expressing virus-specific chimeric IgG. Our data indicate that the antibodies generated are intact and functional.

Therefore, it is an object of the present invention to provide functional full length human antibodies from regions encoding antibody fragments. The humanized antibodies can be used as a therapeutic agent or a diagnostic agent.

It is another object of the present invention to provide vectors for converting Fab antibody fragments into full-length human IgG1 antibody by insect cell expression. Two vectors are described in this application, pIE1-Light and pIE1-Heavy which have been engineered to contain human signal sequences, a human IgG1 constant region, and convenient restriction sites to allow joining of the variable domains of Fab coding regions. After reviewing this application, it is clear that other vectors can be designed, for example, for conversion of antibodies from other species (e.g. mouse, monkey etc.) into full-length chimeric antibodies, without moving away from the concepts described herein.

It is yet another object of the present invention to provide a method for producing human antibodies from Fab coding sequences by inserting Fab-derived light chain antibody genes into pIEI-Light, inserting Fab-derived heavy chain coding sequences into pIEI-Heavy, and expressing these genes in insect cells.

It is still another object of the present invention to provide full length light chain gene from single chain Fv coding regions comprised of only light chain variable domains using pAc-V-Light. The source of the Fv coding regions can be from one or two different antibodies. The human antibodies or chimeric human antibodies can be used as a therapeutic agent or a diagnostic agent. After reviewing this application, it is clear that other vectors can be designed, for example, for expression of antibodies from different species, without moving away from the concepts described herein.

It is yet another object of the present invention to provide a method for producing human or chimeric antibodies from single chain Fv comprising inserting light chain variable coding region into pAc-V-Light, inserting heavy chain variable coding region into pIE1-Heavy, and expressing these genes in insect cells.

It is yet another object of the present invention to treat or prevent diseases or infections by administering a therapeutically or prophylactically effective amount of a human or chimeric antibody of the present invention or a mixture of human or chimeric antibodies of the present invention to a subject in need of such treatment.

It is another object of the present invention to provide passive vaccines for treating or preventing infections or diseases comprising a therapeutically or prophylactically effective amount of the human or chimeric antibodies of the present invention which protect against such infection or disease, in combination with a pharmaceutically acceptable carrier or excipient.

It is yet another object of the present invention to provide a method for diagnosis of infection or disease by assaying for the presence of the infectious agent in a sample using the human or chimeric antibodies of the present invention.

It is still another object of the present invention to provide novel immunoprobes and test kits for detection of infection or disease comprising human or chimeric antibodies according to the present invention. For immunoprobes, the antibodies are directly or indirectly attached to a suitable reporter molecule, e.g., an enzyme or a radionuclide. The test kit includes a container holding one or more antibodies according to the present invention and instructions for using the antibodies for the purpose of binding to an infectious agent to form an immunological complex and detecting the formation of the immunological complex such that presence or absence of the immunological complex correlates with presence or absence of the infection or disease.

It is another object of the present invention to provide anti-idiotypic antibodies raised against one of the present human or chimeric antibodies for use as a vaccine to elicit an active response.

BRIEF DESCRIPTION OF THE DRAWINGS

These and other features, aspects, and advantages of the present invention will become better understood with reference to the following description and appended claims, and accompanying drawings where:

FIG. 1A and 1B represent cassette vectors for conversion of phage display-selected human Fab fragments to full-length mAbs by stable transformation of insect cells. (A) Vector pIEI-light contains Sac I and Not I restriction enzyme sites for insertion of λ or κ light chain genes. (B) Vector pIEI-Heavy contains cloning site Xho I and the coding region for each of the constant domains of human IgG1 (CH1, CH2, CH3) and for a minor 3'-segment of the variable domain (V) of the PUUV-specific human mAb used to engineer the cassette. Restriction enzyme sites Xho I and Apa I, Age I, or Bst XI are used for insertion of heavy chain coding sequences. The cassette vectors contain appropriate light (L) or heavy (H) leader DNA sequences, and both retain the baculovirus immediate early gene promoter, IEI; the ampicillin resistance gene (Amp), the baculovirus enhancer element, hr5; the origin of replication (ori); and polyadenylation sequences (polyA) of the backbone plasmid, p-IEI (Novagen, Inc.).

FIG. 2A and 2B. Cloning light chain genes and heavy chain coding regions of human Fab antibody fragments. (A) λ κ or K light chain genes of pComb3-based human Fabs are cloned into cassette vector pIEI-Light by digestion with Sac I and Not I or by using PCR and specific oligonucleotide primers if the genes are obtained from other phage display systems that do not utilize these sites. (B) To clone heavy chain coding regions of human Fab genes, pComb3-based heavy chain genes of IgG1 Fab fragments are inserted into cassette vector pIEI-Heavy by digestion with Xho I and either Apa I, Age I, or Bst XI. If the heavy chain genes code for other subtypes or classes of antibody or if the genes are obtained from other phage display systems that do not possess these restriction sites, coding sequences for the variable regions of these Fabs can be cloned by PCR using specific oligonucleotide primers that contain the appropriate sites and sequences. In this instance, the reverse primer must begin with the CH1 linker sequence 5'GATGGGCCCTTGGTGGAGGC . . . (SEQ ID NO:1) and be immediately proceeded by the sequence of the precise 3' end of the heavy chain variable coding region.

Figure 3:
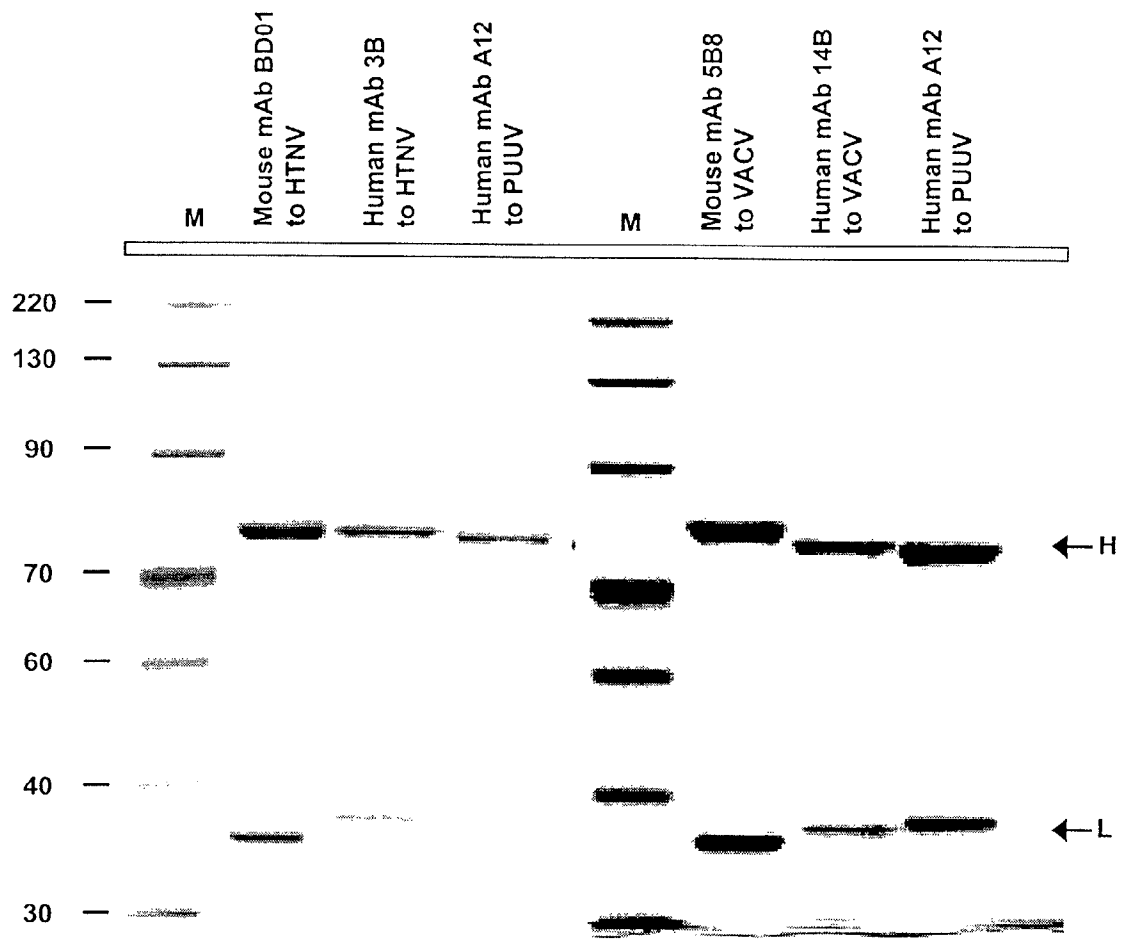

FIG. 3. SDS-polyacrylamide gel electrophoresis and Coomassie blue stain of insect cell-expressed recombinant human IgG. Antibodies were affinity-purified and concentrated from mouse ascitic fluids for mAbs BD01 and 5B8 or from insect cell culture supernatants for human mAbs 3B, 14B, and A12. Heavy (H) and light (L) antibody chains are indicated. The sizes of molecular weight markers (M) are shown to the left of the panel.

FIGS. 4A and 4B. ELISA of insect cell-expressed recombinant human mAbs. Indirect ELISA was performed with twofold dilutions of affinity-purified IgG collected from supernatants of cultured insects cells or from mouse ascitic fluids. (A) Comparison of the binding specificity to HTNV of human recombinant mAb 3B, mouse mAb BD01, and, as a negative control, PUUV specific human mAb A12. (B) Comparison of the binding specificity to VACV of human recombinant mAb 14B, mouse mAb 5B3, mouse mAb 5B8, and, as a negative control, HTNV-specific mouse mAb BD01.

Figure 5:
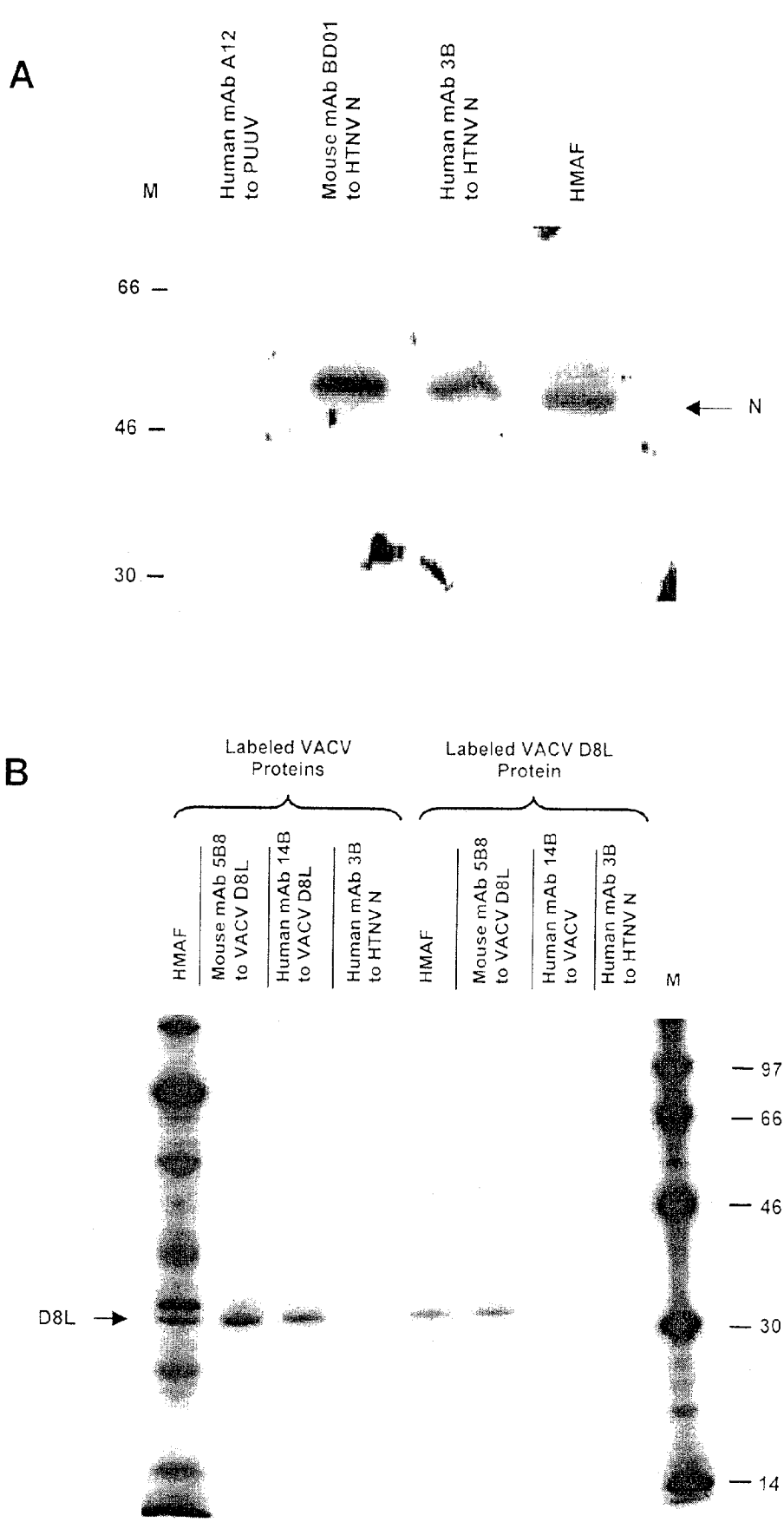

FIGS. 5A and 5B. Immunoprecipitation and polyacrylamide gel electrophoresis of radiolabeled HTNV or VACV proteins with affinity-purified antibodies. (A) HTNV proteins radiolabeled with $^{35}$S-cysteine were immunoprecipitated with mouse mAb BD01, human recombinant mAb3B, hyperimmune mouse ascitic fluid (HMAF) to HTNV, and, as a negative control, human mAb A12 to PUUV. Nucleocapsid (N) is indicated, and the sizes of molecular weight markers (M) are shown to the left of the panel. (B) VACV-infected Vero cells or COS cells transfected with naked DNA vector pWRF/D8L expressing the VACV D8L gene were radiolabeled with $^{35}$S-cysteine, and viral proteins were immunoprecipitated with mouse mAb 5B8, human recombinant mAb 14B, HMAF to VACV, and, as a negative control, human recombinant mAb 3B to HTNV. D8L protein is indicated, and the sizes of molecular weight markers (M) are shown to the right of the panel.

Figure 6:
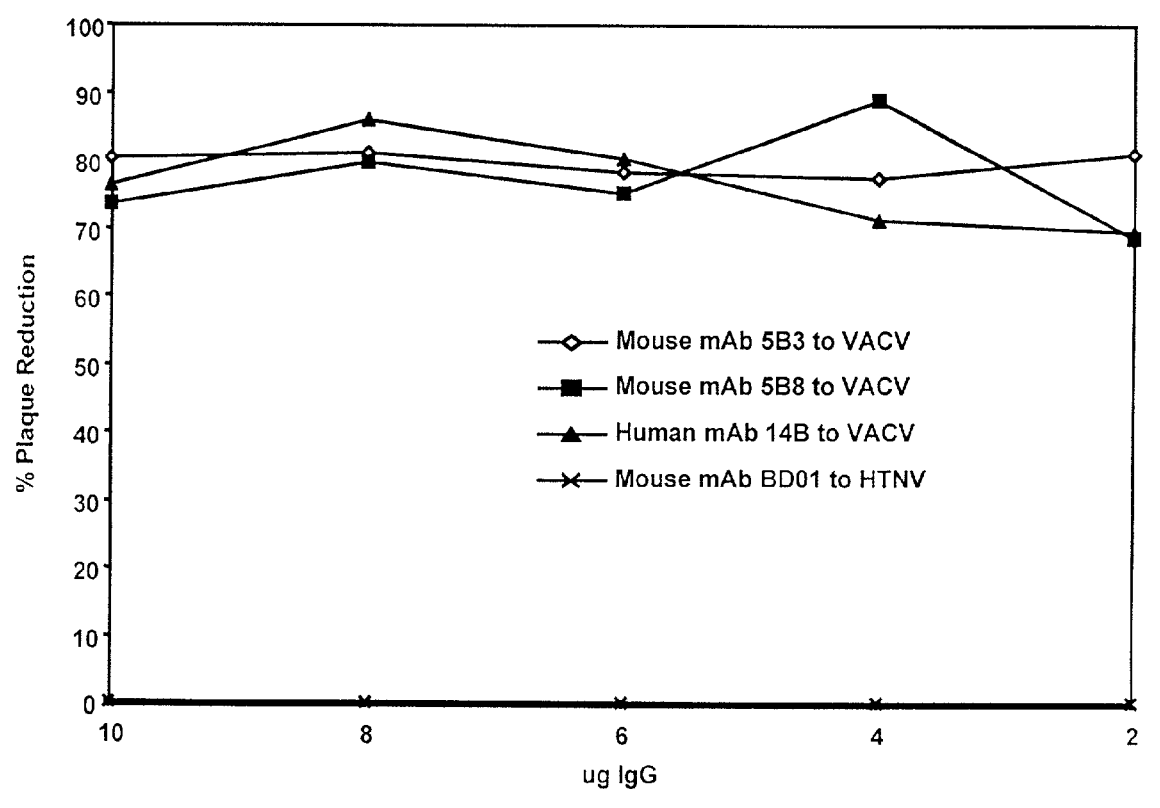

FIG. 6. Plaque reduction neutralization test (PRNT) with VACV and affinity-purified antibodies. Neutralization by insect cell-expressed recombinant mAb 14B was compared to that of mouse mAbs 5B3, 5B8, and, as a negative control, HTNV-specific mAb BD01. PRNT was carried out using purified IgG standardized to 20 ug/ml then diluted accordingly.

Figure 7:
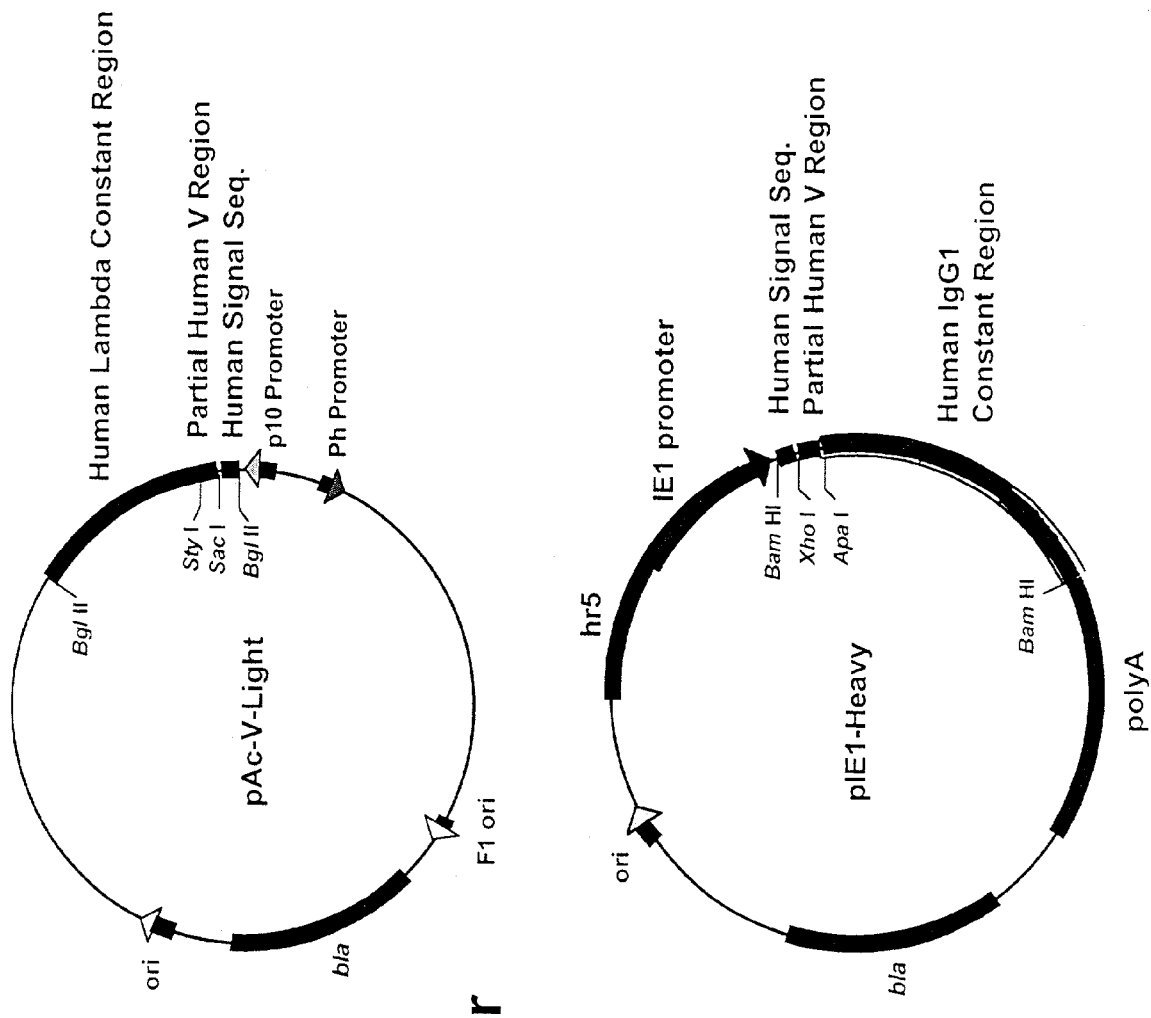

FIG. 7. Cassette vectors for conversion of human or mouse variable regions to complete human or mouse/human chimeric IgG, pAc-V-Light and pIEI-Heavy (described above).

Figure 8:
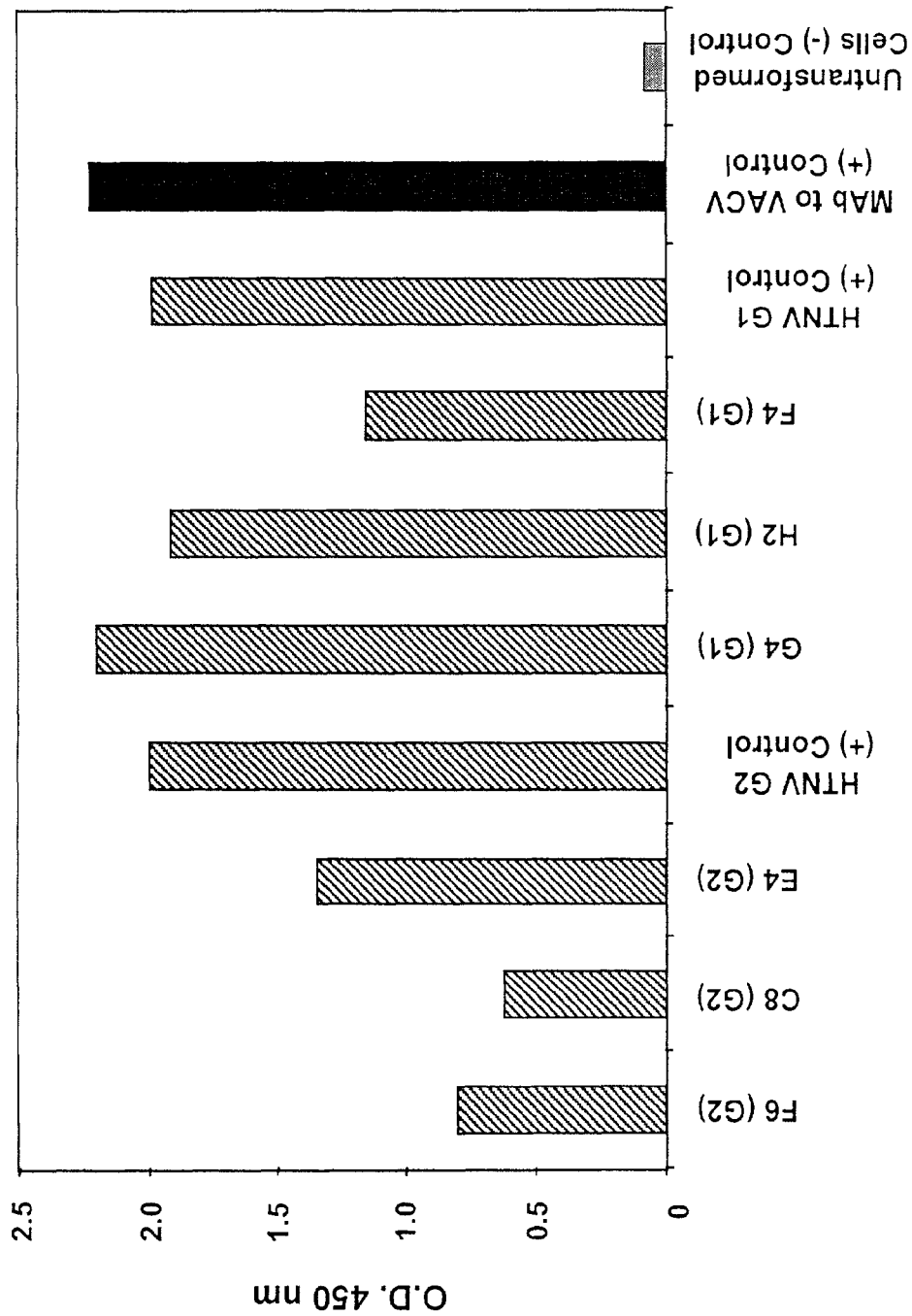

FIG. 8. ELISA of insect cell-expressed mouse/human chimeric MAbs. Insect cells were transfected with plasmids containing chimeric genes coding for IgG to either HTNV G1 or G2. Transformed cells that expressed IgG were identified by ELISA of insect cell culture supernatants. Horseradish peroxidase(HRP)-conjugated, anti-human Fc-specific antibody was used to detect chimeric IgG bound to microtiter plates coated with anti-mouse Fab-specific antibody. Microtiter wells coated with anti-human Fab-specific antibody were used for ELISA of a positive control human MAb to vaccinia virus (VACV), and HRP-conjugated anti-mouse Fc-specific antibody was used to detect positive control mouse MAbs to HTNV G1 and G2. IgG titers for cell lines F6, C8, and E4 as well as G4, H2, and F4 transformed with mouse/human antibody genes coding for MAbs to HTNV G2 and G1 proteins, respectively.

Figure 9:
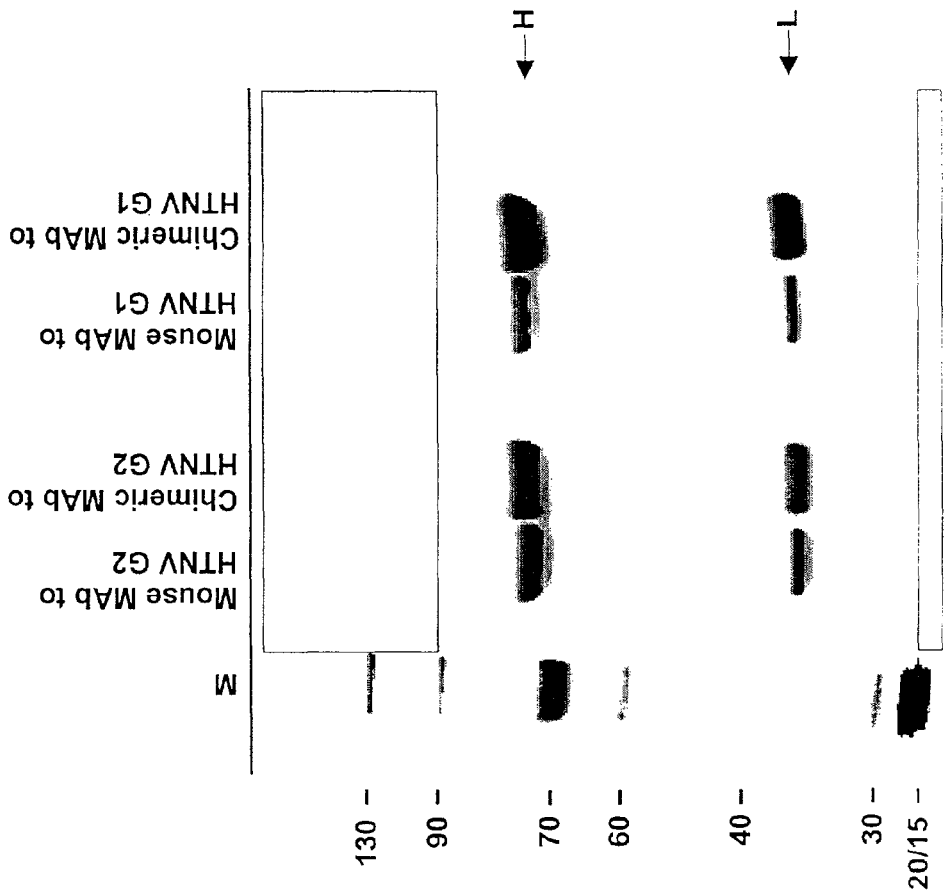

FIG. 9. SDS-PAGE and Coomassie blue stain of chimeric IgG. Coomassie blue-stained mouse MAb to HTNV G2 protein (2), insect cell-expressed chimeric IgG to HTNV G2 protein (3), mouse MAb to HTNV G1 protein (4), and insect cell-expressed chimeric IgG to HTNV G1 protein (5). The heavy (H) and light (L) chains are indicated, and the sizes of molecular weight markers (1) are shown to the left of the panel.

FIGS. 10A and 10B. ELISA with HTNV-specific mouse/human chimeric IgG. Transformed cells expressing HTNV-specific chimeric IgG were evaluated by ELISA of cell culture supernatants using microtiter plates coated with purified HTNV. Bound chimeric IgG was detected with HRP-conjugated, anti-human Fc-specific antibody. The above panel compares the antigen-binding characteristics of HTNV G1- or G2-specific IgG obtained from transformed insect cell lines, using HTNV-specific mouse MAbs as positive controls and a negative control human MAb to VACV.

DETAILED DESCRIPTION

In the description that follows, a number of terms used in recombinant DNA, virology and immunology are extensively utilized. In order to provide a clearer and consistent understanding of the specification and claims, including the scope to be given such terms, the following definitions are provided.

The basic antibody structural unit is known to comprise a tetramer. Each tetramer is composed of two identical pairs of polypeptide chains, each pair having one "light"(about 25 kDa) and one "heavy" chain (about 50-70 kDa). The amino-terminal portion of each chain includes a variable region of about 100-110 or more amino acids primarily reponsible for antigen recognition. The carboxy-terminal portion of each chain defines a constant region primarily responsible for effector function. The variable regions of each light/heavy chain pair form the antibody binding site. Thus, an intact antibody has two binding sites.

Light chains are classified as either kappa or lambda. Heavy chains are classified as gamma, mu, alpha, delta, or epsilon, and define the antibody's isotype as IgG, IgM, IgA, IgD, and IgE, respectively. Within light and heavy chains, the variable and constant regions are joined by a "J" region of about 12 or more amino acids, with the heavy chain including a "D" region of about 10 more amino acids (See generally, Fundamental Immunology, Paul, W., ed. 3rd ed. Raven Press, N.Y., 1993, SH. 9).

Modified antibody: an antibody molecule in which (a) the constant region, or a portion thereof, is altered, replaced or exchanged so that the antigen binding site (variable region) is linked to a constant region of a different or altered class, effector function, and/or species, or an entirely different molecule which confers new properties to the modified antibody, e.g., an enzyme, toxin, hormone, growth factor, drug, and the like; or (b) the variable region, or a portion thereof, is altered, replaced or exchanged with a variable region having a different or altered antigen specificity.

The term "Fab fragment" refers to an antibody molecule comprised of a single complete light chain and the variable domain as well as constant region 1 of a single heavy chain.

The term "phage display" refers to the process by which Fab fragments are generated by bacterial expression of antibody genes and displayed on the surface of filamentous bacteriophage. Briefly, heavy and light chain Fab coding regions are cloned downstream of bacteria leader sequences in phagemid vector, for example, pComb3. Furthermore, the heavy chain coding sequence is cloned in-frame with a gene encoding the carboxyl-terminal portion of a minor bacteriophage coat protein. This allows for the expressed Fab to be tethered via the heavy chian to the inner membrane of the bacterial host. For display of Fabs on the surface of bacteriophage, bacteria transformed with pComb3 constructs are infected with helper phage. When phage pass through the inner membrane following replication, they acquire the coat protein as well as the Fab. Phage displaying Fabs on the surface can then be selected by various screening methods.

The term "substantially pure" or "isolated" means an object species is the predominant species present (i.e. on a molar basis it is more abundant than any other individual species in the composition), and preferably a substantially purified fraction is a composition wherein the object species comprises at least about 50 percent (on a molar basis) of all macromolecular species present. Generally, a substantially pure composition comprises more than about 80, 90, 95, or 99% percent by weight of all macromolecular species present in the composition. Most preferably, the object species is purified to essential homogeneity (contaminant species cannot be detected in the composition by conventional detection methods) wherein the composition consists essentially of a single macromolecular species.

The present invention partly pertains to a method for making human antibodies. For that purpose, three vectors, or expressible genetic constructs were constructed. The expressible genetic constructs of the present invention contain a cassette for the expression of the light or heavy chain of the antibody. In general, the term "cassette" is defined as a DNA fragment containing coding regions necessary for engineering complete antibody genes. For a vector for expression of the light chain, e.g. pIE1-Light, the cassette includes a signal sequence that encodes a peptide that directs secretion of a protein from the host cells such as the human leader sequence and associated restriction enzyme cloning sites for insertion of the DNA sequence encoding the light chain of the desired antibody. For a vector for expression of the heavy chain, e.g. pIE1-Heavy, the cassette includes a signal sequence that encodes a peptide that directs secretion of a protein from the host cells such as the human leader sequence, associated restriction enzyme cloning sites for insertion of the DNA sequence encoding the heavy chain of the desired antibody, and the a coding region for a human constant domain, such as the human constant domain of IgG1. For a vector for expression of the light chain from single chain Fv fragment, e.g. pAc-V-Light, the cassette includes a signal sequence that encodes a peptide that directs secretion of a protein from the host cells such as the human leader sequence, associated restriction enzyme cloning sites for insertion of the DNA sequence encoding the light chain of the desired antibody, and the coding region of a constant domain, such as a human lambda or kappa constant domain. The construct may also contain other advantageous features such as a promoter, an enhancer, a poly adenylation sequence, and/or an expressible selectable marker gene.

The signal sequence that directs secretion of the antibody protein from the host cell may be any DNA segment that confers upon the antibody product the ability to be translocated across the cell membrane such that the product accumulates at high levels in the culture medium. If the signal sequence causes direct protein translocation, it is provided 5' to the antibody gene coding region. It is also envisioned that the antibody may be secreted from the host by vacuolar translocation. In such a case, the signal sequence can be 5' or 3' to the antibody coding region.

The light and heavy chain leader sequences used in the Examples below were obtained from antibody genes for a neutralizing human IgG1 monoclonal antibody to Puumala virus that we described previously (Guttieri et al., 2000, J. Immunol. Methods 246, 97-108; Liang et al., 1997, Virology 235, 252-260), and were shown to function efficiently in insect cells. The light and heavy chain signal DNA sequences were cloned into pIEI-Light and pIEI-Heavy, respectively, by PCR amplification using specific oligonucleotide primers. It was necessary first to obtain the complete DNA sequences of the antibody genes coding for the virus-specific MAb. Once sequence data were obtained, subsequent analysis of these data and of previously published data (Liange et al., 1997, supra) revealed the leader sequences and, thereby, allowed for the design of primers used for PCR amplification. These sequences may also be obtained by in vitro synthesis of the appropriate sequences.

A light chain leader sequence, derived from a lambda light chain antibody gene, was used in pIEI-Light for expression of both lambda or kappa light chain genes. A kappa leader sequence may also be used.

The promoter for antibody encoding genes may be any promoter known to be active in insect host cells. Known insect promoters have generally been shown to work well in a variety of insect host cells. Thus, it is believed that any of the known insect promoters would be acceptable for use in the present invention. The promoter need not necessarily be derived from an insect gene, but may also be obtained from a virus or may be synthesized in vitro. The promoter may be inducible or constitutive. A promoter can further be modified by the addition of enhance elements (e.g. the baculovirus enhancer element hr5 described in the Examples below) that increase or stabilize transcription from the promoter.

The constructs expressible in insect cells described in the present invention include a baculovirus ie1 promoter which promotes transcription of the nucleotide sequence 3' to it in transformed insect cells. In one construct, pIE1-Light (FIG. 1), a human light chain signal sequence has been inserted downstream of the ie1 promoter. This sequence is proceeded by restriction enzyme sites useful for inserting full-length light-chain antibody genes. In another construct, pIE1-Heavy (FIG. 1), a human signal sequence is inserted downstream of the ie1 promoter proceeded by a human IgG1 constant domain and restriction enzyme sites to allow for in-frame cloning of the coding sequences for heavy-chain variable domains of selected Fab fragments. The human signal sequences and the coding region for the IgG1 domain were derived from a human antibody to Puumala virus described previously (Liang et al., 1997, Virology 235, 252-260). Both the Light and Heavy constructs are pIE1-based vectors (Jarvis et al., 1996, Protein Expr. Purif. 8, 191-203; Novagen Inc., Madison, Wis.) and contain the baculovirus enhancer element hr5, an ampicillin resistance gene, and polyadenylation sequences. If desired, the light and heavy chain sequences may be inserted into one vector, however, it would be preferable in this case to ensure that the cassettes are under the control of their own promoters since placing the cassettes under control of a single promoter could reduce efficiency of expression of either gene.

Since we were unable to engineer a vector for generating full-length light chain antibody genes derived from scFv in a pIE1-based vector due to limitations incurred by restriction sites present within the plasmid, it was necessary to find another plasmid with suitable restriction sites that allow to construct the complete gene which can then be transferred into pIE1for expression in insect cells. Hence, pAc-V-Light was engineered as a tool for generating full-length light chain antibody genes derived from scFv fragments. The light chain antibody gene, once generated, must be subcloned from pAc-V-Light into an expression vector for protein expression in insect cells, for example, a pIE1-based vector. It is preferable to transfer the complete light chian antibody gene into pIE1since the fragment can be subcloned using convenient Bgl II sites.

Therefore, according to the present invention, a DNA construct for expressing in insect cells a complete antibody light chain derived from corresponding single chain Fv, is comprised of a transcription terminator functional in insect cells, a human constant light chain region, a DNA sequence which encodes a variable domain of the antibody light chain derived from a single chain Fv fragment, and (preferably subcloned from pAc-V-Light or a similar construct), a promoter that promotes transcription in insect cells.

The terminator sequence that directs the antibody-encoding gene or genes may, likewise, be any sequence known to be active in insect cells that causes the addition of a poly A chain to mRNA. Modifications that increase the number of conserved polyA sequences at the 3' end of the gene or modifications to the nucleotides surrounding the polyA sequence may either enhance polyadenylation or improve upon recognition of the polyA sequence, respectively.

The expressible selectable marker gene, if any, may be any gene that confers a selectable property upon the insect host cells. The marker gene is preferably a gene that confers antibiotic resistance on the otherwise antibiotic-sensitive host cells and allows the monitoring of transfomation. Many such genes are known. The neo gene conferring neomycin resistance is a suitable selectable marker gene, although other genes that confer neomycin resistance or resistance to another drug such as Hygromycin B, Blasticidin, and Zeocin may be used. The selectable marker gene is preferably provided on a separate construct, or to the genetic construct as a single DNA fragment that includes, in addition to the structural gene, a promoter active in insect cells and a terminator sequence for adding a poly A chain to the marker gene mRNA. The promoter and terminator may be any of those known to the art that confer an acceptable level of resistance so that cells that have taken up the genetic construct may be identified and distinguished from untranformed cells. The regulatory elements that direct expression of the antibody encoding gene or genes may also direct expression of the selectable marker gene. In the examples below, the antibiotic resistance gene is provided in a separate construct.

The genetic constructs of the present invention may be transferred into any host cell of insect origin in which the construct is expressible and secretable and from which the desired antibody molecules are secreted. Insect cell lines derived from liepidopteran cells (moths and butterflies) such as *Trichoplusia ni, Spodoptera frugiperda* and others known to people in the art. A suitable and high yielding insect cell line is *Trichoplusia ni* (TN) cell line BTI-TN-5B1-4 commercially available from Invitrogen Corp. (Carlsbad, Calif. ), SF9 cells or SF21 cells (Invitrogen Corp. Carlsbad, Calif.). It would be clear to a person of ordinary skill in the art that certain elements of the vectors can be replaced with other elements available to a person with ordinary skill in the art without altering the essential function or purpose of the construct, for example, the antibiotic resistance marker gene, or for the purpose of adapting the vector to a different cell line or for the expression of antibodies of different species.

A variety of systems can be used in the present invention to introduce the DNA constructs described into insect cells. DNA transfer may be Lipofectin-mediated, may be by an accelerated particle delivery or a cell fusion method, an electroporation method, or by any other method of delivering DNA in an expressible form into a host cell. The Lipofectin-mediated, transfer is the preferred method and is detailed in the Examples below. It is understood that modifications of this protocol are within the ability of one skilled in the art.

A method for producing human antibodies from Fab fragments includes inserting the light chain gene of the desired antibody into the vector pIE1-Light downstream of the promoter of said vector. Similarly, the coding sequence for the heavy chain variable region of the desired antibody can be inserted into the pIE1-Heavy vector. The vectors containing the insertions are then cotransfected into insect cells and the transfected cells are propagated and amplified and the desired antibody is isolated from the transformed cells.

For example, a human light chain antibody gene from phage-display vector pComb3. These genes could also be obtained from other phage display systems that do not utilize phagemid vector pComb3. Alternatively, light and heavy chain antibody genes could be obtained directly from hybridoma cell lines. In both cases, PCR amplification with specific oligonucleotide primers would be required to clone and insert the genes. Please see Examples below for specific methods for obtaining light and heavy chain sequences. Examples of these systems include: lambda expression kits commercially available from Stratagene (La Jolla, Calif.) (e.g. Lambda ZAP Vector Kits) as well as phagemid vector pComb3H or pComb8 (Scripps Research Institute, La Jolla, Calif.). Genes may also be obtained from vectors used for mammalian cell expression, including, for example, commercially availabe vectors pCMV-Script, pDual, and pCMV-TAg1-5 vectors from Stratagene, and a variety of other systems as described by Werner et al. (1998 Drug Res. 48, 870-880) (e.g. vectors pBPV, ptPA/DHFR, pCMV/DHFR, pNEOSPLA, and pEE14). Furthermore, genes could be obtained from baculovirus expression plasmids, including, for example, pACUW51 (Pharmingen, San Diego, Calif.) or pBAC4x-1 vector systems (Novagen, Inc., Madison, Wis.).

Clearly, the light and heavy chain coding regions that comprise the cassettes in pIEI-Light and pIEI-Heavy, respectively, could be excised from these plasmids and inserted into numerous other plasmids for expression in other eukaryotic systems such as those just described for baculovirus or mammalian expression. The light and havy chain coding regions of the cassettes could be easily excised by restriction digestion with Bgl II,for the light chain cassette, and with Bam HI, for the heavy chain cassette, from pIEI-Light and pIEI-Heavy, respectively, and cloned into other expression vectors downstream of appropriate promoters (e.g. the baculovirus polyhedrin or p10 late promoters or the CMV promoter for mammalian expression). In this manner, other individuals could use these cassettes for conversion of Fabs into full-length antibodies by baculovirus or mammalian expression. In addition, the cassettes could be further modified by adding or deleting restriction enzyme sites that would enhance the flexibility of using gene cassettes in other expression systems.

After the light or heavy chain antibody gene is digested with restriction enzymes, the gene fragment is purified. Any method known in the art for isolating and purifying nucleic acids may be used, for example, by gel-purification, Centri-Sep columns (Princeton Separations, Inc., Adelphia, N.J.), Spin-X column purification (Corning Costar Corp.), using DE81 paper (Whatman, Inc.), electroelution (e.g. Jetsorb from PGC Scientific, Gaithersburg, Md.). It is also possible to simply use column purification to purify a sample that has not been subjected to gel electrophoresis.

The gene is ligated into a vector of the present invention digested with appropriate enzymes as is known in the art. Bacterial cells are transformed and screened for transformants containing light chain antibody gene, for example, by using restriction analysis. Any bacterial cell can be used, such as E. coli DH5α cells (Invitrogen, Carlsbad, Calif.), HB101 cells (Invitrogen), or XL1-Blue cells (Stratagene) to name a few.

The coding sequence for human heavy chain variable region is obtained, for example, from phage-display vector pComb3 by digestion with restriction enzymes XhoI and ApaI, AgeI, or BstXI. The purified heavy chain fragment is ligated into vector pIE1-Heavy digested with XhoI and ApaI, AgeI, or BstXI. Bacterial cells are tranformed with the recombinant vector containing the insert, and clones containing coding sequence for heavy chain variable region are screened by using restriction analysis with enzymes XhoI and ApaI, AgeI, or BstXI.

The typical size of each of the light and heavy chain coding sequences cloned into these vectors is approximately 700 bps. Complete light and heavy chain antibody genes are an average size of approximately 750 bp and 1400 bp, respectively.

Figure 2:
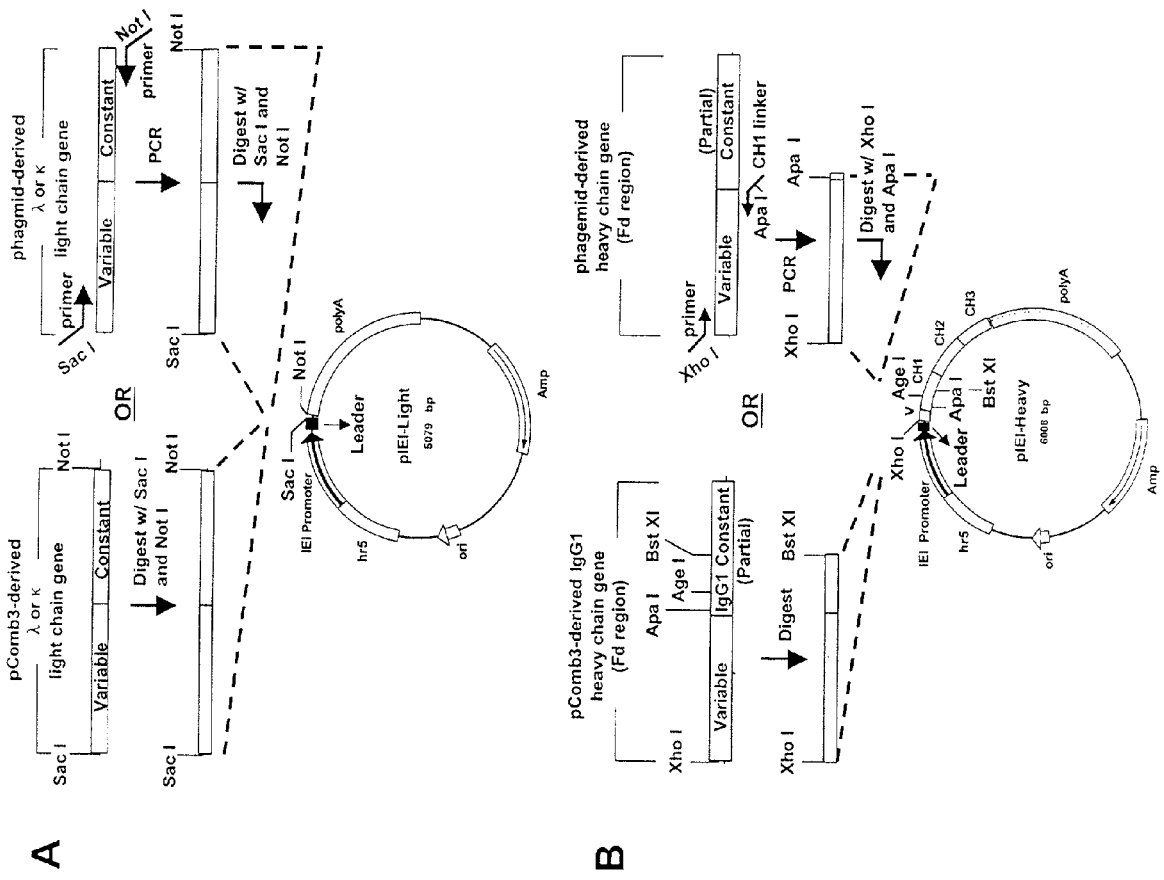

The cloning strategy engineered for this cassette vector system utilizes convenient restriction sites that allow for rapid in-frame cloning of light and heavy chain coding sequences. In other words, the inserts will be cloned in-frame when properly excised from phagemids as described in the Examples below. If PCR is used for cloning, it is necessary that the precise sequences are utilized for primer design to ensure in-frame cloning. Sequences encoding heavy chain V regions of pComb3-derived human Fabs of other subtypes or classes (e.g. IgG2, IgG3, IgGM etc.) can also be cloned in-frame into pIEI-Heavy by PCR amplification using specific oligonucleotide primers (FIG. 2B). To do so, the forward primer must be homologous to the precise 5' end, beginning with the Xho I site, of the sequence coding for the heavy chain V region. The reverse primer must begin with the linker sequence 5' GATGGGCCCTTGGTGGAGGC ... (SEQ ID NO:1) and be immediately proceeded by the sequence of the precise 3' end of the heavy chain V coding region. This linker is complementary to the 5'0 end of the pIEI-Heavy cassette sequence encoding the $C_H1$ constant domain of IgG1 and contains the authentic Apa I site necessary for cloning into the vector. As long as the respective restriction sites and appropriate sequences are included in the primers, PCR can also be used to clone heavy chain V coding regions and light chain genes obtained from other phage display systems.

Using lipofectin reagent (Gibco BRL), insect cells Trichoplusia ni (BTI-TN-5B1-4, Invitrogen, Carlsbad, Calif.) are transfected with the pIE1-cLight containing the complete light chain gene, and pIE1-cHeavy containing the complete heavy chain gene, as well as pIE1-neo (Novagen, Inc.) which confers neomycin resistance or any other plasmid capable of being expressed in insect cells and having the appropriate antibiotic resistance gene. The transfected cells are propagated for two weeks in the presence of selection pressure, e.g. in the presence of antibiotic G418 (Geneticin, Gibco BRL), or until only cells that have received the neo-insert and, therefore, presumably, the antibody genes, survive. After incubation, single colonies are selected to establish clonal cell lines. These cells are expanded until sufficient cell concentrations are available for analysis, usually, about 2-4 weeks. It is known that foreign genes are inserted at multiple sites within the insect cell genome (Jarvis et al., 1990, Biotechnology 8, 950-955). Therefore, it is expected that more than one copy of light and heavy chain genes will be inserted into the insect genome. Clonal cell lines from individual colonies of insect cells are chosen based on the amount of antibody expressed, e.g. based on ELISA titers, and stable growth in culture, i.e., a doubling time of 36-48 hours and a viability of about 90% or higher. The light and heavy chains are assembled in vitro into complete antibodies. Depending upon the level of purity desired, the antibodies can be purified from cell culture supernatants using purification methods known in the art.

Any known technique for purifying the proteins of interest from the culture medium after secretion may be used, such as column affinity purification. However, because the antibody protein secreted accounts for such a high proportion of the total extracellular protein, or an amount readily detectable by ELISA of unpurified cell culture supernatant, the protein may, for certain applications, be used without further purification from other proteins. A stable IgG concentration of approximately 10-60 ng IgG/ml cell culture supernatant can be achieved. Using standard purification techniques, we have been able to achieve an antibody solution which is more than 95% pure.

The assembly pathways used for generation of complete antibody molecules in cells have been extensively studied (see, for example, Scharff, M.,1974, Harvey Lectures, 69:125). In vitro reaction parameters for the formation of IgG antibodies from reduced isolated light and heavy chains have been defined by Beychok, S., Cells of Immunoglobulin Synthesis, Academic Press, New York, page 69, 1979.

The present invention further provides complete functional human antibodies. The functional human antibodies of the present invention have heavy and light chains associated so that the overall molecule exhibits the desired binding specificity and retains the effector functions of the molecule. As discussed previously, the heavy chain portion of the molecule, the constant domains of this chain are extremely important with regard to carrying out the effector functions of the molecule, including complement fixation and opsonization. In addition, certain heavy chain isotypes might elicit greater protection. For instance, it might be more beneficial to use an IgG1 MAb versus an IgG2 when providing treatment against a certain viral infection. Therefore, this cassette vector system may be used to convert an important IgG2 MAb into an IgG1 MAb, i.e. from one heavy chain isotype to a more desirable heavy chain isotype to achieve desirable effector functions.

The present human antibodies are insect cell-expressed antibodies which may exhibit slight differences in glycosylation when compared to their mammalian counterparts. However, these differences do not affect important IgG activities, including complement lysis activity and antibody-dependent cell-mediated cytotoxicity (Boyd et al., 1995, Mole. Immunol. 32, 1311-1318; zu Putlitz et al., 1990, Biotechnology 8, 651-654). In addition, transformed insect cells can provide a continuous and consistent supply of antibody over a long period of time, at least beyond 15 passages (Guttieri et al., 2000, J. of Immunol. Methods, J. of Immunol. Methods 246, 97-108).

The antibodies of the present invention can be utilized in a method for detecting antigens specific for the antibodies in a sample suspected of containing such antigens. The method includes contacting the sample with an antibody which binds an epitope of said antigen, allowing the antibody to bind to said antigen to form an immunological complex, detecting the formation of the immunological complex and correlating the presence or absence of the immunological complex with the presence or absence of said antigen in the sample. The sample can be biological, environmental or a food sample.

The language "detecting the formation of the immunological complex" is intended to include discovery of the presence or absence of the antigen in a sample. The presence or absence of the antigen can be detected using an immunoassay. A number of immunoassays used to detect and/or quantitate antigens are well known to those of ordinary skill in the art. See Harlow and Lane, *Antibodies:A Laboratory Manual* (Cold Spring Harbor Laboratory, New York 1988 555-612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a vaccinee, and an antibody of the present invention, are allowed to compete for binding of the antigen. The amount of antibody bound is then measured, and a determination is made as to whether the serum contains antigen-specific antibodies. This competitive ELISA can be used to indicate immunity to known protective epitopes in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al.,1976 (*Clin. Chim. Acta* 70:1-31), and Schurs, A. H. W. M., et al. 1977 (*Clin. Chim Acta* 81:1-40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid such as serum, plasma, urine, or blood. By "environmental sample" is meant a sample such as soil and water. Food samples include canned goods, meats, and others.

Yet another aspect of the present invention is a kit for detecting an antigen in a biological sample. The kit includes a container holding one or more antibodies which binds an epitope of a antigen to be detected and instructions for using the antibody for the purpose of binding to said antigen to form an immunological complex and detecting the formation of the immunological complex such that the presence or absence of the immunological complex correlates with presence or absence of said antigen in the sample. Examples of containers include multiwell plates which allow simultaneous detection of a desired antigen in multiple samples.

The cassette vector system of the present invention was assayed by converting two human Fabs, one specific for Hantaan virus and the other for vaccinia virus into full-length, functional IgG1 MAbs in transformed insect cells as described in detail in the Examples below.

Given these results, antibodies produced according to the present invention are suitable both as therapeutic and prophylactic agents for treating or preventing infection from an antigen recognized by the antibodies produced in susceptible subjects. Subjects include humans, guinea pigs, hamsters, monkeys, mouse, to name a few.

The antibodies can be used for therapeutic purposes, by themselves, in complement lysis, or coupled to toxins, drugs, immunomodulators, peptide effectors, or therapeutic moeities for targeted delivery of the coupled moeity. For example, the heavy chain cassette of the present invention could be further modified to allow for expression of a fusion protein that consists of an antibody fused to any protein (e.g. toxin) that enhances the therapeutic or prophylactic potential of the antibody. In this manner, the antibody could serve as a tool for delivering a therapeutic reagent to a specific target. To do so, the coding sequence of the cassette, e.g. in pIE1-Heavy, would be modified to contain the in-frame sequence encoding the protein to be fused to the antibody. The present invention could be further manipulated in order to generate antibodies that possess dual-antigen binding specificities. For example, the antigen binding site comprised of one of the light and heavy chains of the antibody could be specific for an epitope that is different than that of the antigen binding site comprised of the other light and heavy chains of the antibody. In this manner, for example, an antibody specific for a receptor on a tumor cell could also bind to a toxin directed against the cell; thereby providing a mechanism for specific delivery of the toxin to the tumor. To generate an antibody such as this by using this system, it would be necessary to co-transfect insect cells with two pIE1-Light vectors that contain light chain genes encoding light chains with the desired specificities and two pIE1-Heavy vectors that contain heavy chain genes coding for heavy chains with the corresponding specificities. Cells expressing an antibody that possesses both specificities would be selected for by various methods, such as subjecting culture supernatants of clonal cell lines with two rounds of affinity purification such that the first round of purification favors selection of antibodies with the first epitope proceeded by a second round of purification favoring the second epitope. The binding specificities for antibodies obtained after this second round could be confirmed by ELISA. In this manner, clonal cell lines expressing the appropriate antibody can be identified and amplified.

The antibodies of the invention can be utilized for passive immunization, especially in humans, without negative immune reactions such as serum sickness or anaphylactic shock.

In general, this will comprise administering a therapeutically or prophylactically effective amount of one or more antibodies produced according to the methods of the present invention to a susceptible subject or one exhibiting an infection or disease related to the antigen recognized by the produced antibodies. The full-length antibodies of the present invention retain the Fc region which mediates important immune functions, including opsonization and complement activation.

Treatment of individuals having an infection or disease may comprise the administration of a therapeutically effective amount of one or more full-length antibodies of the present invention. The antibodies can be provided in a kit as described below. The antibodies can be used or administered as a mixture, for example in equal amounts, or individually, provided in sequence, or administered all at once. In providing a patient with antibodies, or an antibody capable of protecting against infection or disease in a recipient patient, the dosage of administered agent will vary depending upon such factors as the patient's age, weight, height, sex, general medical condition, previous medical history, etc.

The antibodies capable of protecting against an infective agent are intended to be provided to recipient subjects in an amount sufficient to effect a reduction in the infection symptoms. An amount is said to be sufficient to "effect" the reduction of infection symptoms if the dosage, route of administration, etc. of the agent are sufficient to influence such a response. Responses to antibody administration can be measured by analysis of subject's vital signs. In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-i g/kg, 1 g/kg-5 g/kg, 5 g/kg-10 g/kg (body weight of recipient), although a lower or higher dosage may be administered.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

In a similar approach, another therapeutic use of the antibodies of the present invention is the active immunization of a patient using an anti-idiotypic antibody raised against one of the present antibodies. Immunization with an anti-idiotype which mimics the structure of the epitope could elicit an active anti-antigen response (Linthicum, D. S. and Farid, N. R., Anti-Idiotypes, Receptors, and Molecular Mimicry (1988), pp 1-5 and 285-300).

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. A kit for the production of antibodies from Fab fragment would comprise a number of container means containing one or more construct(s) for the production and expression of the light chain gene, e.g. pIE1-Light, and the heavy chain gene, e.g. pIE1-Heavy. A kit for the production of antibodies from scFv would comprise a number of container means containing one or more construct(s) for the production of a complete light chain, e.g. pAc-V-Light, and construct(s) for expressing the light chain in insect cells, e.g. pIE1, as well as one or more construct(s) for expressing the heavy chain gene in insect cells. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means.

The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Virus, Cells, and Plasmids

Hantaan virus (HTNV), strain 76-118 (Lee et al., 1978, J. Infect. Dis. 137, 298-308), was propagated in Vero-E6 cells (ATCC CRL 1586). Vaccinia virus (VACV) Connaught human vaccine strain (derived from the New York City Board of Health strain) (McClain et al., 1997, J. Infect. Dis. 175, 756-763) and strain WR (Western Reserve) (ATCC VR-119) were propagated in Vero cells (ATCC CRL 1587). COS cells (ATCC CRL 1651) were used to obtain radiolabeled VACV-D8L protein for immunoprecipitation studies. Vero, Vero-E6, and COS cells were maintained in Eagle's minimal essential medium supplemented with 10% heat-inactivated fetal bovine serum (FBS), 10 mM HEPES, and antibiotics (100 U/ml penicillin, 100 ug/ml streptomycin, and 50 ug/ml gentamicin) (cEMEM). *Trichoplusia ni* (TN) cell line BTI-TN-5B1-4 (Invitrogen, Carlsbad, Calif.) was used to establish transformed insect cell lines. TN cells were maintained in monolayers as previously described using serum-free Excell-405 medium (JRH Biosciences, Lenexa, Kans.) (Guttieri et al., 2000, J. of Immunol. Methods 246, 97-108). Mouse hybridoma cell line BD01, secreting IgG to HTNV nucleocapsid (N) protein, was described previously (Ruo et al., 1991, Arch. Virol. 119, 1-11). Mouse mAbs from hybridoma cell lines 5B3 and 5B3, secreting IgG to VACV D8L protein, were kindly provided by Dr. Alan Schmaljohn, United States Army Medical Research Institute of Infectious Diseases (USAMRIID), Frederick, Md.

Transfer vectors pIEI-3 and -4 (Novagen Inc., Madison, Wis.) were used as backbone plasmids for construction of heavy and light chain cassette vectors, respectively. Selection plasmid pIEI-neo (Novagen), which confers neomycin resistance, was used in establishing transformed insect cell lines. Naked DNA vector pWRG/D8L, used for immunoprecipitation studies, was kindly provided by Dr. Jay Hooper, USAMRIID, Frederick, Md.

Construction of Cassette Transfer Vectors pIEI-Light and pIEI-Heavy

DNA manipulations were carried out using standard techniques (Sambrook et al., 1989, *Molecular Cloning: A Laboratory Manual,* 2nd ed. Cold Spring Harbor Laboratory Press, New York), with DNA purified by Qiagen Plasmid Maxi or Gel Extraction Kits (Qiagen, Valencia, Calif.). The genetic elements of the cassettes were derived from previously characterized insect cell-expressed, human IgG1 mAb A12 to Puumala virus (PUUV) G2-protein (Guttieri et al., 2000, supra). The complete light and heavy chain antibody genes coding for this mAb were cloned separately into transfer vectors pIEI-3 and pIEI-4, thereby generating pIEI-3L and pIEI-4H, respectively.

The signal DNA sequence of the human lambda, light chain antibody gene in pIEI-3L was amplified by polymerase chain reaction (PCR) and cloned into backbone plasmid pIEI-4 to generate light chain cassette vector pIEI-Light. The forward and reverse oligonucleotide primers used for amplification were SigL/H-F: 5'-CATTGTCCGTGTGCGCTAGCATGCCCGTAA-3'(SEQ ID NO:2) and SigL-R: 5'-TAGTCGCGAGCGAGCTCCTGGGCCCAGGACCCTGTGCAG-3'(SEQ ID NO:3), respectively. Primer SigL/H-F contains authentic cloning site Nhe I and is homologous to plasmid sequences upstream of the multiple cloning regions in pIEI-3 and pIEI-4. Reverse primer SigL-R contains cloning sites Nru I and Sac I and, with the exception of these sites, is homologous to the 3'-end of the light chain leader sequence. Amplification was performed by 30 repeated PCR cycles at 94° C. for 45 sec and 72° C. for 3 min using the DNA thermal cycler 480 system (Perkin-Elmer, Foster City, Calif.) and Pfu DNA polymerase (Stratagene, La Jolla, Calif.), according to the manufacturer's instructions. The PCR product was cloned into Nhe I and Nru I sites in vector pIEI-4, yielding the pIEI-Light cassette comprised of a human leader DNA sequence proceeded by Sac I and Not I light chain cloning sites (FIG. 1A).

To construct the heavy chain cassette vector, a pIEI-4H DNA restriction fragment that contained the coding sequence for each constant domain of human IgG1 was subcloned into backbone vector pIEI-3 by digestion with Bgl II and Not I. For cloning purposes, this fragment also included a minor 79 bp segment of the 3'-coding region for the heavy chain variable (V) domain of the PUUV-specific mAb. The resulting construct, designated pIEI-Heavy, was digested with Bam HI and religated in order to remove redundant Pme I, Nru I, and Not I restriction sites within the pIEI-3 multiple cloning region downstream of the cassette. To complete construction, the human signal DNA sequence of the heavy chain gene in pIEI-4H was amplified by PCR and then cloned into pIEI-Heavy. The forward and reverse primers used for amplification were SigL/H-F, described above, and SigH-R: 5-CGCAGATCTAGCTCGAGCAGTTGCACCTCACACTGGACA-3' (SEQ ID NO:4), respectively. With the exception of Bgl II and Xho I restriction sites, SigH-R is homologous to the 3í-end of the 69 bp heavy chain leader sequence in pIEI-4H. The parameters used for PCR were the same as those described for amplification of the light chain signal sequence. The PCR product was cloned into Nhe I and Bgl II sites upstream of the heavy chain constant region gene in cassette vector pIEI-Heavy. The resultant construct contains the human heavy chain cassette comprised of a leader sequence proceeded by the heavy chain Xho I cloning site and the coding region for a minor 3'-segment of the PUUV-specific V domain followed by the entire coding sequence for the complete IgG1 constant region (FIG. 1B).

Cloning Heavy Chain Coding Regions and Light Chain Genes of Fabs

Two human IgG1 Fab antibody fragments, designated 3 and 14, were selected for conversion to full-length IgG in order to test the efficacy of our cassette vectors. Both Fab 3, specific to HTNV N protein (unpublished data), and Fab 14, specific to a 34-kDa VACV protein (Schmaljohn et al., 1999, Virology 258, 189-200), were previously generated in our laboratory using phagemid expression vector pComb3 (Barbas et al., 1991, Proc. Natl. Acad. Sci. USA 88, 7978-7982). Coding sequences for heavy chain regions and complete light chains of these Fabs were separately cloned into pIEI-Heavy and pIEI-Light, respectively. Specifically, Fab heavy chain gene regions were excised from phagemid pComb3 and inserted into pIEI-Heavy by digestion with Xho I and Bst X1. The corresponding light chain genes of the virus-specific Fabs were sublconed separately into plasmid pIEI-Light by digestion with Sac 1 and Not I. In this manner, 2 pairs of constructs were generated. The first pair, designated pIEI-HTNV-H/L, included the pIEI-Heavy and pIEI-light plasmids containing respective heavy and light chain genes for the HTNV-specific full-length human, IgG1 recombinant mAb. The pIEI-Heavy and pIEI-light plasmids comprising the second pair, designated pIEI-VACV-H/L, contained respective human heavy and light chain genes coding for the complete IgG1 recombinant mAb specific to VACV.

Transformation of Insect Cells and Purification of IgG

To establish transformed insect cell lines expressing complete antibodies, Lipofectin reagent (Gibco-BRL, Grand Island, N.Y.) and previously described methods (Guttieri et al., 2000, supra; Jarvis et al., 1990, Biotechnology 8, 950-955; Joyce et al., 1993, FEBS 335, 61-64) were used to cotransfect TN insect cells with pIEI-neo and either plasmid pair pIEI-HTNV-H/L or pIEI-VACV-H/L. To allow for selection of neomycin-resistant cells, transfected cells were propagated for 2 weeks in TNMFH medium (Summers and Smith, 1987, *A Manual for Baculovirus Vectors and Insect Cell Culture Procedures*. Texas Agricultural Experiment Station Bulletin No. 1555) supplemented with 10% FBS and the antibiotic G418 (Gibco-BRL). After this initial selection, cells were maintained in medium lacking the antibiotic. Individual colonies were selected and amplified to establish clonal cell lines that were then maintained as stationary cultures at 28° C. in Excell 405-medium.

Antibody affinity purification MAbTrap GII kit (Amersham Pharmacia Biotech, Piscataway, N.J.) was used to purify human IgG1 from supernatants of transformed insect cell cultures and mAbs BD01, 5B3, and 5B8 from mouse ascitic fluids. Prior to purification, insect cell culture supernatants were collected 72 hr after cell passage, clarified by centrifugation, and concentrated using Centricon Plus 80 filters (Amicon, Beverly, Mass.). Eluted fractions of affinity-purified IgG were concentrated with Centricon YM-10 filters (Amicon). Antibody concentration was determined by comparison to Coomassie blue-stained bovine serum albumin protein standards and by enzyme-linked immunosorbent assay (ELISA) using known concentrations of purified mAbs for comparison. Approximately 5 ug of each mAb preparation was examined by SDS-polyacrylamide gel electrophoresis (PAGE) in 10% NuPage Bis-Tris gels, according to the manufacturer's specifications (Novex, San Diego, Calif.).

Enzyme-linked Immunosorbent Assay

Capture ELISA was used, as previously described (Guttieri et al., 2000, supra), to detect and titrate complete human IgG1 mAbs secreted by transformed insect cells and to titrate mouse mAbs. Briefly, flat-bottomed 96-well microtiter plates were coated overnight at 4° C. with a 1:1600 dilution of goat anti-human or anti-mouse Fab-specific antibody (Sigma, St. Louis, Mo.) in phosphate-buffered saline (PBS), pH 7.4. After blocking for 1 h with PBS containing 0.05% Tween-20 and 3% skim milk (PBS-TS), 100 ul of two-fold dilutions of insect cell culture supernatants or affinity purified IgG in PBS-TS were added to the wells and incubated for 1 h at 37° C. The plates were then washed four times with PBS containing 0.05% Tween-20 (PBS-T), and bound antibody was detected by 1 h incubation at 37° C with a 1:1600 dilution of horseradish peroxidase-conjugated, anti-human or anti-mouse Fc-specific antibody (Sigma). After washing, TMB peroxidase substrate (Kirkegaard and Perry, Gaithersburg, Md.) was added, plates were incubated at room temperature for 15 min, and results were measured at 450 nm in an automated microplate reader (Bio-Rad, Hercules, Calif.).

Antigen-binding characteristics of insect cell-expressed antibodies were analyzed by indirect ELISA using sucrose gradient-purified HTNV (Schmaljohn et al., 1983, J. Infect. Dis. 148, 1005-1012) or VACV Connaught vaccine strain-infected cell lysates (Schmaljohn et al., 1999, supra). For assays using HTNV, microtiter plates were coated overnight at 4° C. with purified virus diluted 1:200 in carbonate buffer, pH 9.6. The ELISA was then carried out, as described above, using two-fold dilutions of 1.25 ug/ml preparations of affinity-purified mouse mAbs or insect cell-expressed human IgG1 mAbs. To detect specificity to VACV, virus-infected cell lysates were diluted 1:150 in PBS, pH 7.4; added to 96-well microtiter plates (50 ul/well); and dried overnight at room temperature. The antigen-coated plates were blocked for 1 h at 37° C. with PBS containing 0.05% Tween-20, 5% FBS, and 3% goat serum (blocking buffer). After washing with PBS-T, 100 ul of two-fold dilutions of 1 ug/ml preparations of the purified insect cell-expressed human IgG1 mAb or mouse mAbs in blocking buffer were added to the wells, and the ELISA was then continued as described above.

Immunoprecipitation

Affinity-purified mouse mAbs and insect cell-expressed human IgG1 mAbs were used to immuno-precipitate radiolabled authentic HTNV or VACV proteins from infected cell lysates. Radiolabeling and immunoprecipitation were performed as previously described for VACV (Schmaljohn et al., 1999, supra) and HTNV (Liang et al., 1996, Virology 217, 262-271), with modifications. Specifically, Vero or Vero-E6 cells infected with VACV or HTNV, respectively, were labeled for 4 h at 3 days post-infection, and proteins were precipitated with purified IgG using protein A sepharose (CL-4B, Sigma). VACV-specific antibodies were also used to immunoprecipitate radiolabeled VACV D8L protein obtained from COS cells transfected with naked DNA vector pWRG/D8L, according to an established transient expression method (Hooper et al., 2000, Virology 266, 329-339). SDS-PAGE was carried out as described above.

Plaque-reduction Neutralization test (PRNT) Neutralization assays were performed with VACV-infected cell lysate using methods similar to those previously described (Hooper et al., 2000, supra). Briefly, affinity-purified mouse mAbs 5B3 and 5B8 as well as the insect cell-expressed VACV-specific, human IgG1 mAb were standardized to 20 ug/ml, further diluted in cEMEM, and incubated with VACV-infected cell lysate diluted in cEMEM to give approximately 2000 PFU/ml. Virus-antibody mixtures were applied to Vero cell monolayers in 6-well plates for 1 h and then 2 ml of cEMEM was added to each well. After incubation for 3 days at 37° C., monolayers were stained with a 1% crystal violet and 70% ethanol solution. Plaques were counted, and the % reduction in plaque formation was determined by comparison with control wells containing cells infected with VACV incubated with bovine serum albumin.

EXAMPLE 1

Construction of Insect Cell Expression Cassette Vectors pIEI-Light and pIEI-Heavy We engineered two cassette vectors, pIEI-Light and pIEI-Heavy, that allow for conversion of phage display-selected human Fab antibody fragments into full-length IgG1 mAbs by expression in stably transformed insect cells (FIG. 1). These vectors contain convenient restriction sites that, by rapid in-frame cloning, permit joining of the genetic elements of the cassettes to Fab light chain genes and heavy chain coding regions. Using these constructs, full-length antibody genes can be generated and inserted into the insect cell chromosome under control of the baculovirus immediate early gene promoter, IE1. The expression elements of the cassettes were derived from human IgG1 mAb A12 to PUUV that we described previously (Guttieri et al, 2000, supra; Liang et al., 1997, Virology 235, 252-260), and both cassette plasmids are pIEI-based vectors (Jarvis et al., 1996, Protein Expr. Purif. 8, 191-203; Novagen Inc.). In designing these constructs, we created Sac I and Xho I cloning sites in pIEI-light and pIEI-Heavy, respectively, by mutations within the multiple cloning regions of the backbone plasmids. These restriction sites were generated since they are also used to clone light and heavy chain Fab genes into phagemid pComb3 for bacterial expression and phage display. As a result, these sites as well as authentic restriction sites already available in the cassette vectors and in pComb3 can be easily utilized to clone pComb3-derived human Fab coding sequences. In general, cloning sites were also selected based on their low frequency of restriction in human antibody genes (Persic et al., 1997, Gene 187, 9-18).

Cassette vector pIEI-Light contains an authentic 60 bp human signal DNA sequence downstream of the IE1 promoter proceeded by mutated Sac I and authentic Not I cloning sites that are used for insertion of pComb3-based lambda or kappa light chain genes (FIGS. 1A and 2A). In vector pIEI-Heavy, the authentic 69 bp leader DNA sequence of human heavy chain subgroup III is located downstream of the IE1 promoter and is proceeded by mutated cloning site Xho I followed by the coding region for each of the constant domains of human IgG1 (FIG. 1B). Single authentic Apa I, Age I, and Bst X1 restriction sites are located within this cassette at the 5' end of the sequence encoding heavy chain constant domain 1 ($C_H1$) (FIG. 1B). Since heavy chains (Fd regions) of human Fab IgG1 antibody fragments include the CH1 domain, heavy chain coding sequences for these Fabs can be rapidly cloned in-frame from pComb3 into cassette vector pIEI-Heavy by double digestion with Xho I and either Apa I, Age I, or Bst XI (FIG. 2B). Sequences encoding heavy chain V regions of pComb3-derived human Fabs of other subtypes or classes (e.g. IgG2, IgG3, IgGM etc.) can also be cloned in-frame into pIEI-Heavy by PCR amplification using specific oligonucleotide primers (FIG. 2B). To do so, the forward primer must be homologous to the precise 5' end, beginning with the Xho I site, of the sequence coding for the heavy chain V region. The reverse primer must begin with the linker sequence 5' GATGGGCCCTTGGTGGAGGC.(SEQ ID NO:1 ) and be immediately proceeded by the sequence of the precise 3' end of the heavy chain V coding region. This linker is complementary to the 5'end of the pIEI-Heavy cassette sequence encoding the CH1 constant domain of IgG1 and contains the authentic Apa I site necessary for cloning into the vector. As long as the respective restriction sites and appropriate sequences are included in the primers, PCR can also be used to clone heavy chain V coding regions and light chain genes obtained from other phage display systems. Both pIEI-Light and pIEI-Heavy retain the baculovirus enhancer element hr5, ampicillin resistance gene, and polyadenylation sequences of the backbone plasmids.

EXAMPLE 2

Conversion of Human Fab Fragments to Full-length IgG1 mAbs in Stably Transformed Insect Cells To evaluate the efficiency of our cassette vector system, two human Fabs, HTNV-specific Fab 3 and VACV-specific Fab 14, were selected for conversion to complete IgG1 recombinant mAbs. Both Fabs were obtained from phage display libraries generated with phagemid vector pComb3, and both possessed IgG1 heavy chain $C_H$ domains. To generate the complete genes for conversion of these antibody fragments, coding regions in pComb3 were digested with Sac I and Not I, for excision of light chain genes, or Xho I and Bst XI, for heavy chain coding sequences, and the restriction fragments were directly cloned into cassette vector pIEI-Light or pIEI-Heavy, respectively. As a result, a pair of constructs, comprised of pIEI-Light and pIEI-Heavy, was engineered for expression of each complete mAb. To generate insect cell lines producing either the HTNV- or VACV-specific full-length antibodies, TN insect cells were co-transfected with the appropriate plasmid pair and with selection vector pIEI-neo after which cells were propagated under selective pressure with the antibiotic G418. ELISA was then used to detect complete human IgG in transformed cell culture supernatants, and from these data, antibody-secreting TN cell clones were selected for further expansion and analysis (data not shown). In this manner, cell lines HTNV-3B and VACV-14B were established.

To confirm production and secretion of complete light and heavy chains, insect cell expressed-mAbs HTNV-3B and VACV-14B were affinity-purified from cell culture supernatants and examined by SDS-PAGE. Full-length antibody chains of the expected sizes were observed for both recombinant mAbs when compared to insect cell-expressed human mAb A12 to PUUV (Guttieri et al., 2000, supra), used to engineer the cassettes, and to mouse mAbs BD01 and 5B8 specific to HTNV N and VACV D8L proteins, respectively (FIG. 3).

EXAMPLE 3

Biological Function of the Insect Cell-expressed Recombinant Human Antibodies

Previously, immunoprecipitation studies with human Fabs 3 and 14 indicated that the fragments reacted with HTNV N protein (unpublished data) and to a 34-kDa VACV protein (Schmaljohn et al., 1999, supra), respectively. To determine if full-length recombinant mAbs HTNV-3B and VACV-14B retained the ability to bind to their respective target antigens, IgG was affinity-purified from transformed cell culture supernatants and evaluated by indirect ELISA, with purified HTNV or VACV-infected cell lysate. Recombinant mAb 3B reacted with HTNV when compared to mouse mAb BD01, with approximately 100 ng of either antibody required to yield an OD450 in excess of 0.8 (FIG. 4A). Similar results were obtained by ELISA of mAb 14B, using VACV-infected cell lysate and, for comparison, mouse mAbs 5B3 and 5B8 (FIG. 4B). To further evaluate the antigen binding specificities of the recombinant mAbs, we conducted immunoprecipitation studies with radiolabeled HTNV or VACV proteins. Insect cell-expressed mAb 3B immunoprecipitated HTNV N protein as did control mouse mAb BD01 (FIG. 5A). Based upon the predicted size of the VACV protein precipitated by Fab 14 (Schmaljohn et al., 1999, supra), we suspected that recombinant mAb 14B binds to the 34-kDa VACV D8L protein. To confirm this, we conducted immunopreciptiation studies using radiolabeled lysates obtained from cells infected with VACV or cells transfected with a plasmid expressing the D8L gene. As predicted, mAb 14B immunoprecipitated D8L protein when compared to D8L-specific mouse mAb 5B8 (FIG. 5B). We also examined the neutralizing properties of recombinant mAb 14B since previous studies (Schmaljohn et al., 1999, supra) demonstrated that Fab 14 is capable of virus neutralization. Insect cell-expressed mAb 14B retained the ability to neutralize VACV as demonstrated by plaque reduction neutralization tests, with a 70-80% reduction in plaques resulting from the addition of approximately 10 ug of either human mAb 14B or mouse mAbs 5B3 and 5B8 (FIG. 6). These collective data confirmed retention of biological function following conversion of the human Fabs into full-length IgG1 mAbs by transformed insect cell expression using our cassette vectors.

EXAMPLE 4

Cassette Vectors for Conversion of Human or Mouse Variable Regions to Complete Human or Mouse/Human Chimeric IgG pAc-V-Light, a pAcUW51-based (Pharmingen, San Diego, Calif.) vector and previously described pIEI-Heavy contain coding regions for human signal sequences and constant domains for lambda light (pAc-V-Light) and IgG1 heavy chains (pIEI-Heavy) (see FIG. 7). pAc-V-Light contains Sac I and Sty I restriction enzyme sites for insertion of sequences encoding light chain variable domains of antibody fragments. Complete chimeric light chain antibody genes are subcloned into vector pIEI-4 (Novagen, Inc.) for transformation of insect cells. pIEI-Heavy contains Xho I and Apa I restriction enzyme sites for cloning PCR-amplified coding sequences for heavy chain variable regions. Complete chimeric heavy chain genes in pIEI-Heavy are used directly for transformation of insect cells. To test this cassette system, these vectors were used to clone chimeric antibody genes for two MAbs to HTNV G1 and G2 proteins using coding sequences of phage display-selected mouse Fabs. Constructs containing the complete chimeric antibody genes were subsequently used to establish transformed insect cell lines that express the HTNV-specific mouse/human antibodies.

Insect cells were transfected with plasmids containing chimeric genes coding for IgG to either HTNV G1 or G2. Transformed cells that expressed IgG were identified by ELISA of insect cell culture supernatants (FIG. 8). Horseradish peroxidase(HRP)-conjugated, anti-human Fc-specific antibody was used to detect chimeric IgG bound to microtiter plates coated with anti-mouse Fab-specific antibody. Microtiter wells coated with anti-human Fab-specific antibody were used for ELISA of a positive control human MAb to vaccinia virus (VACV), and HRP-conjugated anti-mouse Fc-specific antibody was used to detect positive control mouse MAbs to HTNV G1 and G2. FIG. 8 displays IgG titers for cell lines F6, C8, and E4 as well as G4, H2, and F4 transformed with mouse/human antibody genes coding for MAbs to HTNV G2 and G1 proteins, respectively.

The insect cell-expressed IgG were detected by SDS-PAGE and Coomassie blue staining. FIG. 9 shows Coomassie blue-stained mouse MAb to HTNV G2 protein (2), insect cell-expressed chimeric IgG to HTNV G2 protein (3), mouse MAb to HTNV G1 protein (4), and insect cell-expressed chimeric IgG to HTNV G1 protein (5). The heavy (H) and light (L) chains are indicated. Heavy and light chains of the expected sizes were observed by this analysis, thereby confirming antibody secretion and the intergrity of the expressed antibody chains.

Transformed cells expressing HTNV-specific chimeric IgG were evaluated by ELISA of cell culture supernatants using microtiter plates coated with purified HTNV (FIGS. 10A and 10B). Bound chimeric IgG was detected with HRP-conjugated, anti-human Fc-specific antibody. The antigen-binding characteristics of HTNV G1- or G2-specific IgG obtained from transformed insect cell lines were compared using HTNV-specific mouse MAbs as positive controls and a human MAb to VACV as a negative control. By this analysis, we determined that the full-length chimeric antibodies retained the ability to bind to their respective target antigens.

These collective data confirm the efficacy of the cassette vector system, comprised of pAc-V-Light and pIE1-Heavy, for conversion of scFv fragments into full-length chimeric antibodies that retain their antigen binding capabilities.

What is claimed is:

1. A plasmid vector for expressing in insect cells a complete antibody light chain obtained from a corresponding Fab fragment, wherein said vector is pIE1-Light.

2. A plasmid vector for expressing in insect cells a complete antibody heavy chain obtained from a corresponding Fab fragment, wherein said vector is pIE1-Heavy.

3. A method for obtaining a conformationally active IgG1 antibody from a Fab fragment comprising:

transforming insect cells concurrently with (i) a plasmid vector comprising in 5' to 3' order, a promoter that promotes transcription in insect cells, a signal sequence which directs secretion of a protein from insect cells, restriction enzyme sites for inserting a DNA sequence encoding a light chain variable region and a light chain constant region obtained from said Fab fragment and a transcription terminator functional in insect cells, wherein a DNA sequence which encodes a light chain variable and constant domain obtained from said Fab fragment has been inserted in said restriction enzyme sites, and (ii) a plasmid vector comprising in 5' to 3' order, a promoter that promotes transcription in insect cells, a signal sequence which directs secretion of a protein from insect cells, restriction enzyme sites for inserting a DNA sequence encoding a heavy chain variable region and a heavy chain constant region 1 obtained from said Fab fragment, a complete IgG 1 constant region, and a transcription terminator functional in insect cells, wherein a DNA sequence which encodes a heavy chain variable domain obtained from said Fab fragment has been inserted in said restriction enzyme sites, selecting transformed insect cells that have acquired said plasmid vectors, culturing the transformed insect cells under conditions such that the IgG 1 antibody is produced and secreted, and isolating the IgG1 antibody.

4. The method of claim 3 wherein the plasmid vector in (i) is pIE1-Light and the plasmid vector in (ii) is pIE1-Heavy.

5. The method of claim 3 wherein the insect cells are TN cells.

6. An insect cell transformed with the plasmid vector pIE1-Light.

7. An insect cell transformed with the plasmid vector pIE1-Heavy.

8. An insect cell transformed with the plasmid vectors pIE1-Light and pIEI-Heavy.

9. A kit for obtaining a conformationally active IgG1 antibody from a corresponding Fab fragment comprising:

(i) a plasmid vector for expressing in insect cells a complete antibody light chain obtained from the corresponding Fab fragment, comprising in 5' to 3' order, a promoter that promotes transcription in insect cells, a signal sequence which directs secretion of a protein from insect cells, a DNA sequence which encodes the variable and constant domain of the antibody light chain obtained from a Fab fragment and a transcription terminator functional in insect cells, and (ii) a plasmid vector for expressing in insect cells a complete antibody heavy chain obtained from the corresponding Fab fragment, comprising in 5' to 3' order, a promoter that promotes transcription in insect cells, a signal sequence which directs secretion of a protein from insect cells, a DNA sequence which encodes the variable domain of the antibody heavy chain obtained from an Fab fragment, a complete IgG1 constant region and a transcription terminator functional in insect cells.

10. The kit of claim 9 wherein said plasmid vector in (i) is pIE1-Light and said plasmid vector in (ii) is pIE1-Heavy.

* * * * *